(12) United States Patent
Leclerc et al.

(10) Patent No.: US 7,641,896 B2
(45) Date of Patent: Jan. 5, 2010

(54) ADJUVANT VIRAL PARTICLE

(75) Inventors: Denis Leclerc, Fossambault-sur-le-lac (CA); Nathalie Majeau, Fossambault-sur-le-lac (CA); Constantino III Roberto López-Macías, México D.F. (MX)

(73) Assignee: Folia Biotech Inc., Quebec City (CA)

( * ) Notice: Subject to any disclaimer, the term of this patent is extended or adjusted under 35 U.S.C. 154(b) by 598 days.

(21) Appl. No.: 10/609,417

(22) Filed: Jul. 1, 2003

(65) Prior Publication Data

US 2005/0048082 A1 Mar. 3, 2005

Related U.S. Application Data

(60) Provisional application No. 60/393,659, filed on Jul. 5, 2002.

(51) Int. Cl.
*A61K 35/00* (2006.01)
(52) U.S. Cl. .................. 424/93.1; 435/5; 424/201.1; 424/202.1
(58) Field of Classification Search .................. None
See application file for complete search history.

(56) References Cited

U.S. PATENT DOCUMENTS

| 5,420,026 | A | 5/1995 | Payne |
| 5,958,422 | A | 9/1999 | Lomonossoff |
| 5,977,438 | A | 11/1999 | Turpen et al. |
| 6,042,832 | A | 3/2000 | Koprowski et al. |
| 6,232,099 | B1 | 5/2001 | Chapman et al. |
| 6,544,779 | B1 | 4/2003 | Cichutek |
| 6,627,202 | B2 | 9/2003 | Murray |
| 7,018,826 | B1 | 3/2006 | Hildt |
| 2007/0166322 | A1 | 7/2007 | Leclerc |

FOREIGN PATENT DOCUMENTS

| EP | 1006123 | 6/2000 |
| EP | 1167530 | 1/2002 |
| WO | WO 87/01386 | 3/1987 |
| WO | WO 92/03537 | 3/1992 |
| WO | WO 96/12027 | 4/1996 |
| WO | WO 97/39134 | 10/1997 |
| WO | WO 98/08375 | 3/1998 |
| WO | WO 99/18220 | 4/1999 |
| WO | WO 99/50424 | 10/1999 |
| WO | WO 00/06717 | 2/2000 |
| WO | WO0118199 | 3/2001 |
| WO | WO 01/26682 | 4/2001 |
| WO | WO 01/27282 | 4/2001 |
| WO | WO 01/66778 | 9/2001 |
| WO | WO 01/73078 | 10/2001 |
| WO | WO02/00169 | 1/2002 |
| WO | WO 02/04007 | 1/2002 |
| WO | WO 02/102410 | 12/2002 |

OTHER PUBLICATIONS

Brennan et al. Cowpea Mosaic Virus as a Vaccine Carrier of Heterologous Antigens Molec. Biot. 2001; 17:15-26.*
Igietseme et al. "Antibody regulation of T-Cell Immunity: implications for vaccine strategies against intracellular pathogens" Exp Rev. Vaccines 2004; 3, 1:23-34.*
Gajewski et al. "'Anergy' of TH0 Helper T Lymphocytes Induces Downregulation of TH1Characteristics and a Transition to a TH2-like Phenotype" J. Exp.Med. 1994; 179:481-491.*
Lee-Shanok, Construction and preliminary characterization of papaya mosaic virus as an expression vector for the presentation of foreign epitopes, Thesis for Degree of Master of Science, University of Toronto, 1999, p. 1-108.*
Trembley et al. FEBS Journal, 2006, vol. 273, pp. 14-25.*
Bach 1994 Endocrine Reviews 15(4):516-542.
Bachmann MF et al. 1993 Science 262:1448-1451.
Bachmann MF et al. 1996 Immunology Today 17(12):553-557.
Baratova et al. 1992 Virology 188: 175-180.
Belanger et al. 2000 The FASEB Journal 14:2323-2328.
Blanco et al. 1993 Scand. J. Infect. Dis. 25:73-80.
Brennan et al. 1999 Journal of Virology 73(2):930-938.
Cooke et al. 2001 Nature Immunol. 2(9):810-815.
Cruz et al 1996 Proc. Acad. Natl. Sci. U.S.A. 93:6286-6290.
Cryz 1999 Berna: A Century of Immunological Innovation Vaccine 17:S1-S5.
Dalsgaard et al. 1997 Nature Biotech. 15:248-252.
Daniel et al. 1996 Proc. Acad. Natl. Sci. 93:956-960.
Gonzalez et al. 1993 Microbiol. Immunol. 37(10):793-799.
Gonzalez et al. 1995 Arch. Med. Res. 26:S99-S103.
Grinna et al. 1989 Yeast 5:107-115.
Ikegami R. Papaya Mosaic Potexvirus as an Expression Vector for Foreign Peptides, Thesis Obtained for the Degree of Master of Science, University of Toronto, 1995.
Isibasi et al. 1992 Vaccine 10(12): 811-813.
Isibasi et al. 1988 Infect. Immun. 56(11):2953-2959.
Isibasi et al. 1994 Ann. New York Acad. Sci. 730:350-352.
Kawamura et al. 1986 J. Immunol. 136(1):58-65.
Koprowski et al. 2001 Vaccine 19:2735-2741.
Kratz 1999 Proc. Acad. Natl. Sci. U.S.A. 96:1915-1920.
Leclerc et al. 1998 The J. Biological. Chem. 273(4): 29015-29021.
Leclerc et al. 1999 Journal of Virology 73(1):553-560.
Leclerc et al. 2001 Virus Genes 22(2):159-165.
Levine et al. 1999 Vaccine 17:S22-S27.
Makino et al. 1980 Exp. Anim. Jan. 29(1):1-3.
Maldonaldo et al. 2000 Archives of Medical research 31:S71-S73.
Marusic et al. Sep. 2001 J. of Virology 75(18):8434-8439.

(Continued)

*Primary Examiner*—Larry R Helms
*Assistant Examiner*—Agnieszka Boesen
(74) *Attorney, Agent, or Firm*—Todd L. Juneau

(57) ABSTRACT

The present invention relates to an immunogen-carrier having immunopotentiating or adjuvant properties. More particularly, the immunogen-carrier is a virus-like particle (VLP) from the family of potexvirus, and most particularly the papaya mosaic virus. The VLP produced by recombinant techniques is in fusion with one of its own proteins a protein immunogen. The above VLP and a protein or a protein extract from a viral, bacterial or parasital pathogen may be used as a vaccine.

35 Claims, 9 Drawing Sheets

OTHER PUBLICATIONS

Medzhitov et al. 2000 Seminars in Immunology 12:185-188.
Netter et al. 2001 Journal of Virology 75(5): 2130-2141.
Pang et al. 1998 Trends Microbiol. 6:131-133.
Parriagua-Solis et al. 1995 Immunol. Infect. Dis. 5:244-249.
Plotkin et al. 1995 Arch. Intern. Med. 155:2293-2299.
Porta et al. 1998 Reviews in Medical Virology 8:25-41.
Robins et al. 1984 J. Infect. Dis. 150(3):436-449.
Saier, M.H. Mol. Microbiol. 35(4):699-710, 2000.
Savory et al. 1995 615-634.
Scorer et al. 1993 Gene 136:111-119.
Scott, J.K. et al. 1990 Science 249(4967):386-390.
Simone et al. 1999 Diabetes Care 22(Suppl. 2)B7-B15.
Sit et al. 1993 J. of General Virology 74:1133-1140.
Sit et al. 1989 J. Gen. Virol. 70:2325-2331.
Taylor et al. 1999 Science 285:107-109.
Terskikh, A.V. et al. 1997 Proc. Acad. Natl. Sci. USA 94:1663-1668.
Tian et al. 1996 Nat. Med. 2(12):1348-1353.
Turpen et al. 1995 Bio/technology 13:53-57.
Usha et al. 1993 Virology 197:366-374.
Wong et al. 2001 J. Virol. 75:1229-1235.
Chiu et al. Typhoid Fever in Children, The Lancet vol. 354, p. 2001, Dec. 4, 1999.
Cohen, The Scientific Challenge of Hepatitus C, Science, vol. 285, p. 26, Jul. 2, 1999.
Roitt, The Recognition of Antigen, Chap 4, p. 65-84, 1991.
Schultz, Bacterial Porins: STRX & FNCN, Curr. Opn in Cell Biology, 1993 5:701-707.
Tschopp, High Level Secretion of Glycosylated Invertase in . . . Yeast, Nature Biotech vol. 5 pp. 1305-1308, Dec. 1987.
Sedlik, In Vivo Induction of a Hi Avidity Hi Freq. T Lympho Response . . . Immunity, J. Virology, Jul. 2000, p. 5769-5775.
Storni, Critical Role for Activation of APC in Priming Cytotox T Cell . . . VLP, J. Immunology 2002 168:2880-2886.
Lopez-Marcias et al. Ann. NY Acad. Sci. 1995 772:285-288.
J. Gen. Virol 1993 74:1133-1140, Tim Sit et al. Infectious RNA transcripts derived from cloned cDNA of papaya mosaic virus: effect of mutations to the capsid and polymerase proteins.
J. Gen. Virol 1993 74:1133-1140, Tim Sit et al. Infectious RNA transcripts derived from cloned cDNA of papaya mosaic virus: effect of mutations to the capsid and polymerase pr.
M.S. Thesis, Botany, Univ. Toronto, Richard Ikegami, 1995, "Papaya Mosaic Protexvirus as an Expression Vector for Foreign Peptides".
Sit, T.L., "Nucleotide Sequence of Papaya Mosaic Virus RNA," J. gen. Virol. 70, 2325-2331 ( 1989 University of Toronto, Ontario).
Abouhaidar, M. G., "Nucleotide Sequence of the Capsid Protein Gene and 3' Non-coding Region of Papaya Mosiac Virus RNA," J. gen. Virol., 69, 219-226 (1983 Toronto).
MA Guang-Shu, "The Research Advance of Virus Diseases in the Cucurbitaceae," Heilongjiang Agricultural Science, (1): 44-47 (2001).
Abouhaidar, M.G. et al. The initiation of papaya mosaic virus assembly. Virology 90(1):54-59 (1978).
Abouhaidar, M.G. et al. Nucleotide sequence of the 3'-terminal region of clover yellow mosaic virus RNA. J. Gen. Virol. 70:1871-1875 (1989).
Ruedl, C., et al. Cross-presentation of virus-like particles by skin-delivered CD8(-) dendritic cells: a dispensable role for TAP. Eur. J. Immunol. 32(3):818-825 (2002).
Stubbs, G. Tobacco mosaic virus particle structure and the initiation of disassembly. Phil. Trans. R. Soc. Lond. B 354:551-557 (1999).
Wong, et al."Detection of diverse Hepatitis C Virus (HCV)-specific Cytotoxic TLymphocytes in peripheral blood of infected persons by . . . ".J.Virol.75(3):1229-1235(2001).
Zhang, H., et al. Crystallization and preliminary X-ray analysis of papaya mosaic virus coat protein. J. Mol. Biol. 234(3):885-887 (1993).
Co-pending U.S. Appl. No. 11/556,578, Adjuvant Viral Particle, LeClerc.
Tang et al., (Recent advances in DNA vaccine of hepatitis virus. Hepatobiliary & Pancreatic Dis. Inter., 2002, vol. 1, pp. 228-231.
Machuca et al. Intervirology 1999. vol. 42 p. 37-42.
Letvin. 2006. Nature Immunology. vol. 6, p. 930-939.
Jager et al. (Clinical Cancer Vaccine Trials. Current Opinion in Immunlogy, 2002, vol. 14, p. 176-162.
Pumpens, Paul, et. al., Evaluations of HBs, HBc, and frCP Virus-Like Particles for Expression of Human Papillomavirus 16E7 Oncoprotein Epitopes, *Intervirology*, 2002; 45:24-32.
Fagan, Elizabeth A., et. al., Hepatitis B Vaccine: Immunogenicity and Follow-Up Including Two Year Booster Doses in High-Risk Health Care Personnel in a London Teaching Hospital, *Journal of Medical Virology*, 1987, 21:49-56.

* cited by examiner

A

B

A

B

7,641,896 B2

ADJUVANT VIRAL PARTICLE

BACKGROUND OF THE INVENTION (a) Field of the Invention

The present invention relates to a viral particle bearing immunogens and having immunopotentiation or adjuvant activity. The invention particularly relates to recombinant viral particles and method for enhancing an immune response in a human or an animal by means of these particles.

(b) Description of Prior Art

Vaccination is the most efficient method to fight against infectious diseases. The appearance of new viral diseases (e.g. Hepatitis C virus, Human immunodeficiency virus), and the resistance of pathogenic bacteria (*Salmonella typhii*) to antibiotics are alarming. Vaccination thus become an efficient alternative to help controlling these diseases.

Over the last past 15 years, genetic engineering allowed the precise identification of protein fragments that are responsible for the protective immune response. Therefore, new vaccination strategies emerged. Immunisation of animals with appropriate immunogenic peptides allowed the production of neutralising antibodies that can control diseases. The expression of those immunogenic peptides in heterologous systems provided the basis of subunit vaccines.

Although it has been demonstrated that chemically synthesised oligopeptides are capable of stimulating the production of antibodies against the protein from which they are derived, the peptides themselves have generally been found to be insufficiently immunogenic to serve as vaccines. This is why there has been considerable interest in developing epitope-presentation systems, in which the peptide sequence is fused to a carrier molecule capable of assembly into a macromolecular structure.

Specific immunity can be enhanced by the use of immunopotentiators, such as adjuvants, when administering an antigen to a host. The immune response is mediated by a variety of cells in the immune system. There are two types of immune response: humoral immunity mediated by antibodies, and cellular immunity mediated primarily by cytotoxic T lymphocytes. Antigen presenting cells ("APC") process and present antigen to both B and T cells. B cells secrete specific antibodies as a result of activation and T cells either become helper cells to the humoral response or cytotoxic cells and directly attack the antigen. Adjuvants have been shown to augment these immune responses.

Initial presentation of an antigen induces both IgM and IgG antibodies, forming the primary response. This production of antibodies may fall off, however, over time. A secondary response, which principally involves the production of IgG antibodies, may be triggered by the secondary or later in time presentation of the antigen. A secondary or even primary response, however, is not guaranteed merely by priming the host with an antigen.

A difficulty often encountered in the administration of an antigen is the extent to which the immune system will respond. Certain antigens are not very immunogenic in that upon administration they provoke a weak primary response or no response at all. In such cases, the immune system may not respond to a secondary challenge, and for example, the host may suffer from the disease or condition that the immunization with the antigen was designed to prevent.

In such situations, it is common to give a physiological response modulator ("PRM"). A PRM generally is defined as an immunopotentiating compound. It may be derived from bacteria, such as *Bordella pertussis* or *Corynebacterium parvum*. PRM also may include chemicals, such as polynucleotides, physiologically active molecules, such as thymic hormones, and adjuvants.

Adjuvants are compounds which enhance the immune systems response when administered with antigen producing higher antibody titres and prolonged host response. Commonly used adjuvants include Incomplete Freund's Adjuvant, which consists of a water in oil emulsion, Freund's Complete Adjuvant, which comprises the above with the addition of *Mycobacterium tuberculosis*, and alum. The difficulty, however, in using these materials in humans, for example, is that they are toxic or may cause the host to develop lesions at the site of injection.

Another approach was described by Kawamura and Berzofsky in J. Immunol., 136:58 (1986). In this approach, anti-Ig antibodies, which are reactive with immunoglobulins present on certain B cells, were conjugated to ferritin and myoglobin, and were administered to mice with Incomplete Freund's Adjuvant. Immunogenicity of the mixture was improved, but there was no indication of the immunogenicity of the mixture without the addition of the adjuvant. Also, whilst adjuvants such as Freund's complete adjuvant, Freund's incomplete adjuvant and Montanide can greatly enhance the immune response to an antigen, they suffer from some disadvantages. When used with an antigen in an injectable form, large lesions often form at the site of injection, a situation which renders them unsatisfactory for such use in humans, pets or in meat animals. Furthermore, these adjuvants fail to act as immunopotentiating agents when administered orally or enterally.

It is know in the art that carriers of immunogen or antigens of different nature can be relatively easily genetically engineered. Plant virus are those systems that can be produced in plants and are easily adapted to this application. Cowpea mosaic virus (CPMV), tobacco mosaic virus X (TMVX), and alfalfa mosaic virus (AIMV) are known to having been modified for the presentation of epitopes of interest. Another plant viral vector, potato virus X (PVX), a member of the potexvirus group, is known to tolerate carriage of a complete protein overcoat. Also, U.S. Pat. Nos. 6,232,099 and 6,042,832, International Patent applications published under number WO 97/39134, WO 02/04007, WO 01/66778, WO 02/00169, and EP application 1167530, all describe different variations of virus-like particles carrying foreign proteins in fusion with endogenous proteins. However, nowhere in these references it is mentioned that such particles have any immunopotentiation or adjuvant properties.

Considering the state of the art described herein, there is still a great need for compounds and carrier particles allowing a strong immunization of human and animals while avoiding the use of adjuvants and second vaccinations as actually practiced.

SUMMARY OF THE INVENTION

One aim of the present invention is to provide an immunogen-carrier complex having an immupotentiation property, consisting of a viral-like particle (VLP) carrying at least one immunogen in fusion with a protein or fragment thereof of said VLP, that may be used in the preparation of a composition for inducing an immune response against the protein or fragment thereof.

Another aim of the present invention is to provide a composition comprising a viral-like particle (VLP) and a protein or an extract derived from a virus, bacteria or parasite, that may be used as a vaccine.

In accordance with the present invention there is also provided a method for immunopotentiating an immune response in a human or an animal which comprises administering to said human or animal an immunogen-carrier consisting of a viral-like particle (VLP) carrying at least one immunogen in fusion with a protein or fragment thereof of said VLP, or administering a VLP or a fragment thereof concomitantly with an antigen not directly linked to said VLP.

The present invention also relates to polynucleotide encoding a immunogen-carrier complex consisting of a viral-like particle (VLP) carrying at least one immunogen in fusion with a protein or A polynucleotide encoding a immunogen-carrier complex consisting of a fragment thereof of said VLP, or a VLP alone, said immunogen-carrier complex having the capacity of being assembled when expressed in a plant cell, an animal cell or a microorganism.

The invention also provides for the use of a papaya mosaic virus as an adjuvant.

For the purpose of the present invention the following terms are defined below.

The expression "chimeric protein" is created when two or more genes that normally code for two separate proteins recombine, either naturally or as the result of human intervention, to code for a protein that is a combination of all or part of each of those two proteins.

The expression "fusion capsid protein" means a fusion protein in which one of the genes in the fusion codes for a plant virus capsid protein.

The expression "protective immunity" as used herein is intended to mean the ability of an animal, such as a mammal, bird, or fish, to resist (delayed onset of symptoms or reduced severity of symptoms), as a result of its exposure to the antigen of a pathogen, disease or death that otherwise follows contact with the pathogen. Protective immunity is achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Mucosal immunity can be stimulated by an oral vaccine. The primary result of protective immunity is the destruction of the pathogen or inhibition of its ability to replicate itself.

The expression "humoral immunity" as used herein means the result of IgG antibodies and IgM antibodies in serum.

The expression "cellular immunity" as used herein can be achieved through cytotoxic T lymphocytes or through delayed-type hypersensitivity that involves macrophages and T lymphocytes, as well as other mechanisms involving T cells without a requirement for antibodies.

A "recombinant virus" is one in which the genetic material of a virus has combined with other genetic material.

The terms "polypeptide" or "peptide" as used herein is intended to mean a molecule in which there is at least four amino acids linked by peptide bonds.

The expression "viral nucleic acid" as used herein may be the genome (or a majority thereof) of a virus, or a nucleic acid molecule complementary in base sequence to that genome. A DNA molecule that is complementary to viral RNA is also considered viral nucleic acid. An RNA molecule that is complementary in base sequence to viral DNA is also considered to be viral nucleic acid.

The term "virus-like particle" (VLP) as used herein refers to self-assembling particles which have a similar physical appearance to virus particles and includes pseudoviruses. Virus-like particles may lack or possess dysfunctional copies of certain genes of the wild-type virus, and this may result in the virus-like-particle being incapable of some function which is characteristic of the wild-type virus, such as replication and/or cell-cell movement.

The term "vaccine" as used herein is intended to mean the fusion protein, any particle of which that protein is a part, or any preparation such as plant material of which that protein is a part.

The term "immunopotentiator" as used herein is intended to mean a substance that, when mixed with an antigen, enhances immunogenicity or antigenicity and provides a superior immune response. It will be recognized that it can enhance the expression of co-stimulators on macrophages and other antigen-presenting cells.

DESCRIPTION OF PREFERRED EMBODIMENTS

Figure 1:
FIG. 1 illustrates an electron micrograph of purified PapMV.

In accordance with the present invention, there is provided a virus-like particle carrying immunogen in fusion with endogenous viral proteins, therefore forming a new type of immunogen-carrier being also capable of immunopotentiation or having an adjuvant effect.

In one embodiment of the present invention, there is provided a class of carriers which when linked genetically to an immunogen or hapten can enhance the host's immune response to the immunogen or hapten regardless of whether the complex is administered parenterally, enterally or orally. In addition their use does not result in the formation of large lesions at injection sites.

Accessory cells such as macrophages, B lymphocytes, and dendritic cells are essential for the induction of T cell-dependent immune responses. Accessory cells present antigens to MHC-restricted T cells and produce membrane-associated and secreted costimulators that enhance the proliferation and differentiation of T lymphocytes. Therefore, the presence of competent accessory cells stimulates T cell-dependent immune responses, and their absence leads to deficient responses. Resting macrophages and naive, unstimulated B lymphocytes sented by such antigen-presenting cells (APCs)

may fail to stimulate naïve CD4+ T cells, and may even induce T cell tolerance. In contrast, dendritic cells and activated macrophages and B cells do express costimulators, as well as high levels of APCs. A mechanism of action of the immunogen-carrier of the present invention, is to enhance the expression of costimulators on macrophages and other APCs. Because of this, the administration of immunogens or protein antigens with the immunogen carriers of the invention, acting simultaneously as an adjuvant, promotes cell-mediated immunity and T cell-dependent antibody production. Immunogens are most effective for generating systemic immunity when administered coupled together with an immunogen-carrier of the present invention.

In a first embodiment, the invention provides a complex comprising an immunogen coupled to a carrier virus-like particle (VLP), such that the carrier molecule causes the immune response of a host to the immunogen to be enhanced when the complex is administered to said host, wherein the immunogen may comprise either an antigen or a hapten and the carrier molecule comprises an integral particle of a virus. More particularly, the virus of the present invention is a plant virus.

One way to obtain a good response of B cells is to present the antigen in an organized manner. It is shown that repetitively arranged epitopes cross-link to B cell receptor efficiently and induce a prompt T-independent IgM response followed later by an IgG response. Therefore, a good strategy to increase the immunogenicity of the epitopes and the recognition and presentation to the immune system is the expression of the immunodominant epitopes in an organized fashion like on the surface of a plant virus like PapMV. Particularly, PapMV filfils several characteristics of a good adjuvant and carrier because it is a phylogenetically distant antigen, it is exogenous to the mammal immune system, it is molecularly very complex and it is an organized structure that has a high molecular weight.

It has been surprisingly recognized by the applicant that a crystalline and repetitive structure is not only recognised by the innate immune system, but has in addition an adjuvant effect on the immune system of an immunized host.

In one embodiment of the present invention, there is provided a method in which the use of benign high copy number rod-shaped viruses, preferably plant viruses such as papaya mosaic virus (PapMV), produce immunogen connected to viral coat protein subunits. When assembled, the virus particles comprise long helical arrays of more than 1000 identical fusion proteins (which are typically coat protein—foreign protein fusion molecules) per virion. Generally, the immunogen portion will be displayed on the outer surface of the virus particles.

According to the present invention, the structure of the capsid proteins of plant and animal viruses fulfil these requirements and can be engineered to present immunogenic peptides derived from the pathogen or other sources with which a vaccine-adjuvant is produced. The coat protein of papaya mosaic virus (PapMV), for example, but without limiting it thereto, is an excellent candidate for the development of such a immunogen-carrier-immunopotentiator. This virus harbours a crystalline rod shape and is very repetitive (1200 copies of the same subunit per virion). Recent immunization experiments with PapMV indicate that this virus induces a very strong immune response in mice and is an excellent vector for the development of a vaccine. This immunogen carrier virus can be engineered with several immunogenic peptides of the HCV surface envelope proteins, such as for example, *Salmonella typhii* peptides derived from the porin protein, and with the peptide α9-23 of insulin. The assembly of fusion coat proteins carried by virus like particles (VLPs) are defined as an immunogen-carrier having adjuvant or immunopotentiating properties.

According to the present invention, it is possible to immunopotentiate, or boost an immune reaction against a given antigen. It is known particularly that small molecules often act only poorly as immunogens in their ability to elicit antibodies in an in vivo system. When attached to a immunogen-carrier virus of the present invention, that itself is antigenic, it will give rise to improved antibody response to the smaller molecule. The small molecule attached to the immunogen-carrier in this system, may be called a hapten or antigen, and can vary in size from small to quite large. In one example of this combination, of interest to the health care field, a small portion of the Hepatitis B surface antigen, comprising a sequence of determined amino acids, which is not itself antigenic, can be covalently bound to the VLP, keyhole limpet immunogen-carrier, and the resulting conjugate elicites antibodies in an in vivo system that may cross-react with the native surface antigen of the VLP and also strongly with the whole hepatitis virus. This system of immunogen-carrier can be the basis for an effective vaccine against a disease for which the hapten or antigen codes.

In the present invention, there are provided certain novel immunogen-carriers, as described below, which are conveniently produced by recombinant DNA techniques, which are useful in providing univalent as well as multivalent immunogenic vaccines, and which employ the immunogen-carrier concept described above.

An immunogen is coupled to a carrier VLP to form an immunogen-carrier complex and may then be used in a host in order to provoke an immune response. The immunogen may be specific or recognised for surface structures on T cells, B cells, NK cells and macrophages but not for Class I or Class II APC associated cell surface structures.

The immunogen to which the carrier VLP is coupled may comprise peptides, haptens, carbohydrates, proteins, nucleic acids, and part of viruses, bacteria, parasites and other whole microorganisms. Regardless of the immunogen selected, it must be coupled to the carrier VLP in such a way as not to interfere with the recognition of the immunogen by the host's immune system as an antigenic entity.

The immunogen-carrier complex may be used as a vaccine to raise an immune response in the host. The complex initially may be given in an appropriate dosage in order to elicit an immune response. This may be followed by boosting with the complex or immunogen alone. A variation of this approach may include the formation of one or more immunogen-carrier complexes wherein one or more forms of an immunogen are coupled to one or more carrier VLPs and a plurality of such complexes is administered.

The purpose of administering the immunogen-carrier complex is to provide protection to the host in the form of immunity to the antigen and to avoid the use of adjuvants which have undesired side affects.

In one embodiment, the antigen may be as small an immunogen as a hapten or may be relatively large, such as part of a virus. The size and type of antigen is not critical to the practice of this invention. Any antigen may be used for which an immune response is desired in a host. The invention is especially useful, however, for small weakly immunogenic haptens.

Once the immunogen-carrier complex or complexes are formed, the complex or complexes may be administered to the host. The administration regime need not differ from any other generally accepted vaccination programs. A single administration in an amount sufficient to elicit an effective immune response may be used. Alternatively, other regimes of initial administration of the complex followed by boosting with antigen alone or one or more complexes may be used. Similarly, boosting with either the complex or antigen may occur at times that take place well after the initial administration if antibody titres fall below acceptable levels.

A further embodiment of the present invention is that as the VLPs have a regular multivalent and true helical structure which can be more immunogenic than aggregation of protein or free subunits of proteins, it can be easily assembled from an encoding nucleic acid. Also the greater stability of the particle can provide a long lasting exposure of the immunogen portion to the immune system.

The virus portion on which the immunogen is attached, is preferably disposed on the outer surface of the VLP. Thus where the particle is derived from PapMV, the carrier's portion can be disposed on the amino or carboxy terminus, or inserted in an internal loop disposed on the outer surface of the CP. This can result in improved assembly as compared with the assembly of particles having a second portion on another location of the CP, and can enhance immune recognition of the second portion on the particle surface.

In one embodiment of the present invention, the development of peptide vaccines using a plant viral vector allows to mass-produce vaccines under safe conditions. As much as 1 gram of recombinant virus per kilogram of fresh infected leaves is expected with the recombinant PapMV.

In another embodiment of the present invention, the administration of 200 µg of recombinant virus, or immunogen-carrier complex, which corresponds to 14 µg of peptide, can be sufficient for immunization. One hectare of infected papaya can then potentially be sufficient for the vaccination of 5 million patients. Furthermore, to grow plants is cheap and efficient. Agriculture is the cheapest way to produce a biomass because it does not necessitate sophisticated equipment.

The virus or pseudovirus can be assembled in the host cell to produce infective virus particles which comprise nucleic acid and fusion protein. This can enable the infection of adjacent cells by the infective virus or pseudovirus particle and expression of the fusion protein therein.

The host cell can be infected initially with virus or pseudovirus in particle form (i.e. in assembled rods comprising nucleic acid and a protein) or alternatively in nucleic acid form (ie RNA such as viral RNA; cDNA or run-off transcripts prepared from cDNA) provided that the virus nucleic acid used for initial infection can replicate and cause production of whole virus particles having the chimeric protein.

The first (viral) portion of the fusion protein may be any protein, polypeptide or parts thereof, derived from a viral source including any genetically modified versions thereof (such as deletions, insertions, amino acid replacements and the like). In certain embodiments, the first portion will be derived from a viral coat protein (or a genetically modified version thereof). Mention may be made of the coat protein of Papaya Mosaic virus as being suitable for this purpose. A fusion protein molecule can assemble with other fusion protein molecules or with wild-type coat protein into a immunogen-carrier virion.

In a preferred embodiment of the invention, the particle is derived from a potyvirus or even more preferably a potexvirus such as PapMV, and in such an embodiment, the second portion is preferably disposed at or adjacent the C-terminus of the coat protein. In PapMV, the C-terminus of the coat protein forms a domain on the outside of the virion.

Preferably, a polynucleotide coding for the immunogen portion is inserted at or adjacent a terminus of the polynucleotide coding for the viral portion, such that upon translation, the fusion protein has the viral portion at one end and the immunogen portion at the opposite end. It is not necessary for the viral portion to comprise a whole virus cost protein, but this remains an alternative choice.

A virus or pseudovirus genetically modified to express the fusion protein forms a further embodiment of the present invention, as does any host cell infected with such a virus or pseudovirus.

Preferably, the host cell used to replicate the virus or pseudovirus is a bacteria, where the virus is a plant virus, although plant cells, insect cells, mammalian cells and bacteria can be used with viruses which will replicate in such cells. The cell is preferably a bacterium such as $E.\ coli$ although other forms of bacteria and other cells may be useful, such as cells mentioned above. The cell may be a natural host cell for the virus from which the virus-like particle is derived, but this is not necessary.

According to a particular embodiment of the present invention, the whole virus-like particle is used for stable and long lasting presentation of peptide epitopes for the vaccination of animals.

According to another embodiment of the present invention, PapMV and PapMV virus like particles appear to be very stable and can be stored easily at room temperature. They resist very high temperature and adverse conditions since plant viruses has evolved to resist very difficult conditions that we find in the environment. This is a very important advantage when the vaccine must reach people that are living in poor countries, in regions where access is difficult or for the storage of a diagnostic test for a long period.

Alternatively, the VLP described herein can be used alone as immunopotentiator or adjuvant to enhance an immune response in humans or animals against targeted antigens. It is preferable that the adjuvant or immunopotentiating VLP be administered concomitantly with the antigen against which an immune response must be raised. However, the adjuvant VLP can be administered previously or subsequently to, depending on the needs, the administration of the antigen to patients, humans or animals.

The present invention will be more readily understood by referring to the following examples which are given to illustrate the invention rather than to limit its scope.

EXAMPLE I

Preparation of Immunogen-carrier VLP

The avidity of the affinity peptides selected from the panning process described herein will be improved by multimerisation of the peptides. The multimerisation will be done at the surface of papaya mosaic virus (PapMV) that is a member of the potexvirus group. PapMV has a rod-like structure that is made by assembly of the CP subunits. One virus particle contains 1200 subunits. We will make a fusion of the selected peptide with the PapMV CP. The fusion will be made to expose the peptide to the surface of the PapMV particles after in vitro assembly from a PapMV CP expressed and purified from an $E.coli$ expression system. The assembly of the viral CP then ensured multimerisation of the peptide and has considerably improved avidity.

Figure 2:
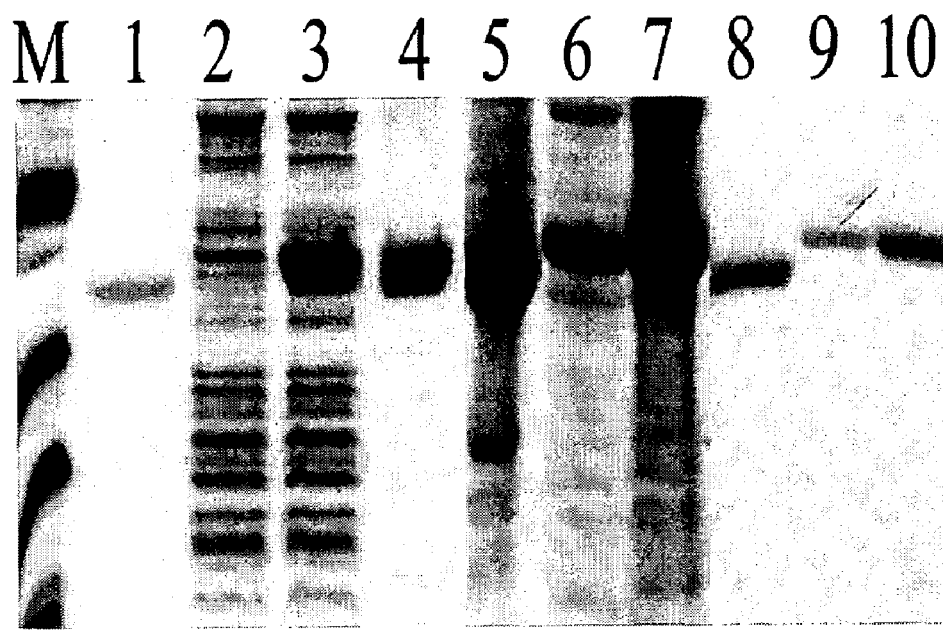
FIG. 2 illustrate tricine SDS-PAGE analysis of the PapMV CP(A) and immunogold laveling showing that the fusion is exposed at the surface of the PapMV VLP (B)
Figure 2:
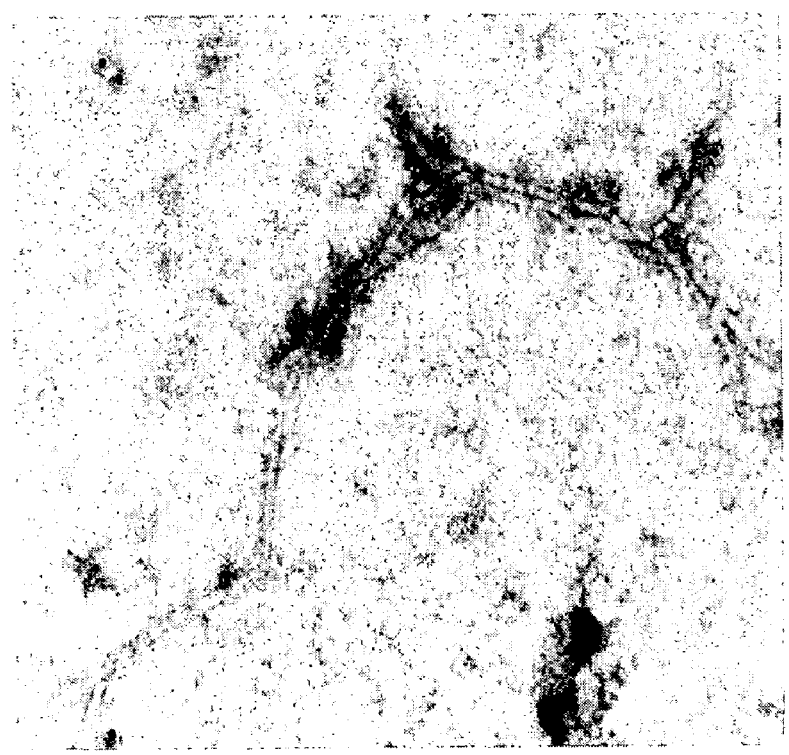

Coat protein (CP) gene was cloned and developed an in vitro assembly system using the coat protein (CP) of papaya mosaic virus (PapMV) (FIG. 1). The CP of PapMV was produced in $E.coli$ in large amount (FIG. 2a) and produced in vitro PapMV virus-like particles that are very similar to the wt virus (FIG. 2b). It is shown for the first time that a recombinant PapMV CP can assemble in virus-like particles in vitro.

Fusion of several peptides to the C-terminus of the CP is allowed by assembly in vitro and gives rise to virus-like particles that are wider than the wt virus because of the fusion (FIG. 3).

EXAMPLE II

Immunopotentiation Effect of Immunogen-carrier VLP

An adjuvant is often used in order to increase the immune response of a candidate vaccine. The enhancement of the inflammatory response favours the migration of more phagocytes to the injection site which, in turn results in an improved antigen presentation by antigen-presenting cells (APC). Allun, emulsions, microparticles and cytokines such as GM-CSF have all been used to increase the immune response of the candidate vaccine. It was confirmed that PapMV induced by itself an inflammatory episode, thus eliminating the need for additional adjuvants. The air pouch model was used to examine whether PapMV induced a proinflammatory event in vivo. In this model, sterile air is injected under the dorsum of mice at days 0 and 3. At day 7, proinflammatory agents can be injected into the air pouch and the inflammatory response measured. This model closely represents subcutaneous injection sites.

Injection of PapMV into the murine air pouch resulted in the accumulation of approximately $8.5\times10^6$ leukocytes, compared to $0.8\times10^6$ leukocytes in vehicle-injected mice (PBS) (FIG. 4). Neutrophils (85%) and monocytes (15%) accumulated in the air pouch 6 hours after injection of PapMV. While quantities as low as 1 μg of PapMV were sufficient to induce the accumulation of leukocytes, maximal accumulation occurred when 100 μg of PapMV was injected. This accumulation was similar to the one induced by injection of 1 μg of LPS, a powerful proinflammatory factor. These results clearly demonstrate that PapMV can efficiently induce an inflammatory episode. This observation shows clearly that the PapMV is perceived by the immune system which, induces signalling and recruitment of cells involved in the defence of our organism. It is likely that PapMV induces signalling through innate immunity.

Furthermore, it was shown in the present experiment that PapMV induces a strong and long lasting humoral response in mice (FIG. 5). 10 mice were injected with three concentrations of PapMV; 1, 10 and 100 αg. Primary antibody response in BALB/c mice immunised with PapMV was efficiently induced independently of the route of immunisation (FIG. 5). High titres were detected at day 5 after immunisation. A classic curve of a primary IgM response was observed. Around day 20, IgM response was absent, even after boosting mice with more viruses. IgG response in immunised mice follows a classic kinetics. High titers of anti-PapMV were detected at day 12 after immunisation and proportionally increased after boosting with this virus. Analysis of IgG isotypes showed a preference in the production of IgG2b and IgG1 during the primary and secondary phase of the Ab response. IgG3 increased titres during the memory phase of the ab response. These data shows that PapMV is able to induce an efficient Ab response in mice. Primary and secondary responses were efficiently induced as well as a long lasting Ab memory. The preferential production of IgG1 suggests a preferential release of IL-4. IL-4 favours class switching to this kind of IgG. Therefore a balance towards TH2 response could be envisaged in these mice. The lack on IgG2a indicates the absence of IFN-α release, since this cytokine has been involved directly in class switching towards this IgG isotype.

Taken together, these data showed the capacity of PapMV to induce an efficient and long lasting antibody response. This result suggests that PapMV particles are excellent vector for the development of a humoral vaccine. The fusion of an immunogen of interest to the VLP will then be recognised as well by the immune system and trigger a strong immune response to the epitope of interest.

Also, it was found that PapMV VLPs migrate specifically to the lymph nodes and the spleen after intraperitoneal or subcutaneous injection in Balb/C mice (FIG. 6). This result indicates that PapMV VLPs are excellent carriers because they migrate efficiently to the sites of emergence of the immune response.

Experimental data demonstrate that the PapMV-antigen induces an efficient antibody response in mice (FIG. 5). In fact, primary and secondary responses are efficiently induced as well as a long lasting antibody memory (FIG. 6). Several immunization routes produced efficiently large amounts of antibodies. Only oral immunization did not result in an immune response. It is likely that the NaHCO3 used to neutralize the acid of the stomach damaged the virus particles and affected the immunogenicity of the particles. IgG1, IgG2a, IgG2b and IgG3 were present even 350 days after one injection of 100 μg of PapMV (FIG. 6). Because IgG2a and IgG3 are present and persist, we can deduce that a TH1 response is induced with PapMV. This suggests that PapMV particles are excellent vectors for the development of an immune humoral response to a foreign antigen. The fusion of an epitope of interest to the PapMV-particle should help to trigger a humoral immune response against the epitope of interest.

Experimental data using the air pouch model in mice dorsum demonstrated that PapMV enhances the inflammatory response and favors the migration of phagocytes to the inoculation site (FIG. 6). This result confirms that PapMV induces by itself an inflammatory episode, thus eliminating the need for additional adjuvant strategies aiming at improving antigen presentation by antigen-presenting cells. Similar results were obtained with virus-like particles (VLPs) harboring the fusion of specific peptides generated in vitro from recombinant proteins (FIG. 6). The recruitment was very fast since we observed the maximum of cells between 6 to 9 hours after the treatment (data not shown). Furthermore, PapMV-particles are efficient to induce an immune response to ovalbumin, a protein known to be non-immunogenic (FIG. 7). This was established by injecting mice (Balb/C) by intraperitoneal route with 2 mg of Ovabulmin, a protein known to be a very weak immunogen, or in combinaison with 50 or 100 αg of PapMV. We injected 6 mice per treatment and collected samples at 0, 4, 8, 12 and 20 days after the injection. Only one injection was made for each treatment. We detected a two times stronger immune response to ovalbumine in presence of PapMV even if ovalbumine is a weak immunogen.

These observations demonstrate that PapMV-particles are rapidly perceived as foreign by the mammalian immune system, which in turn induces signaling and recruitment of cells involved in the defense of the organism.

EXAMPLE III

Hepatitis C Virus as Vaccination Target

Hepatitis C virus (HCV) is a plus strand RNA virus that causes acute and chronic liver diseases. The acute phase of infection is generally associated with mild symptoms but it can lead to cirrhosis and hepatocellular carcinoma. More than 170 million people worldwide are infected, which is 4 times as many as for HIV. In the next few years, the number of deaths from HCV associated diseases may even surpass the death rate caused by AIDS. At the present time, current therapies against HCV are unsatisfactory. The only available therapy is interferon (IFN), but most HCV are resistant because of an inhibition of the interferon inducible protein kinase (PKR) by HCV E2 protein.

It is known that 20% of infected HCV patients naturally clear the virus. This observation suggests that the immune system can eliminate the viruses if it reacts efficiently. It also suggests that we could help the chronically infected patients if we boost their immune system with a therapeutic vaccine against HCV that could help to clear the viral infection by raising neutralizing antibodies to the virus.

Figure 3:
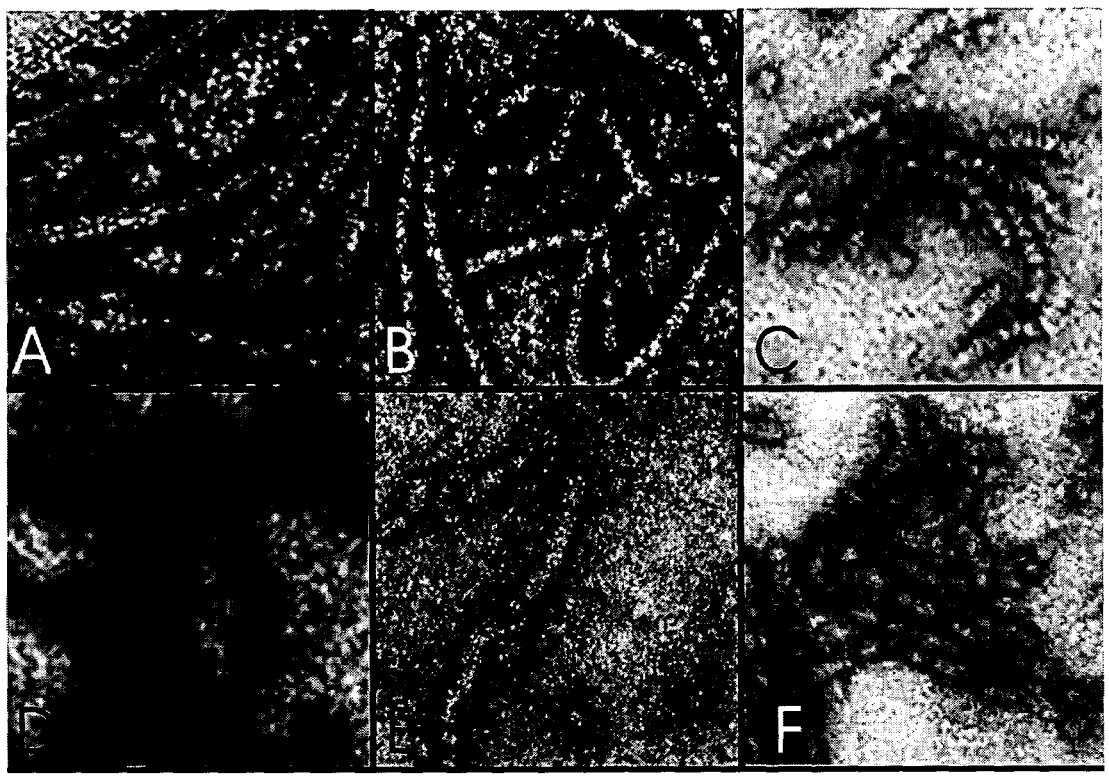
FIGS. 3A to 3G illustrate electron micrographs of PapMV and PapMV VLP assembled in vitro.
Figure 4:
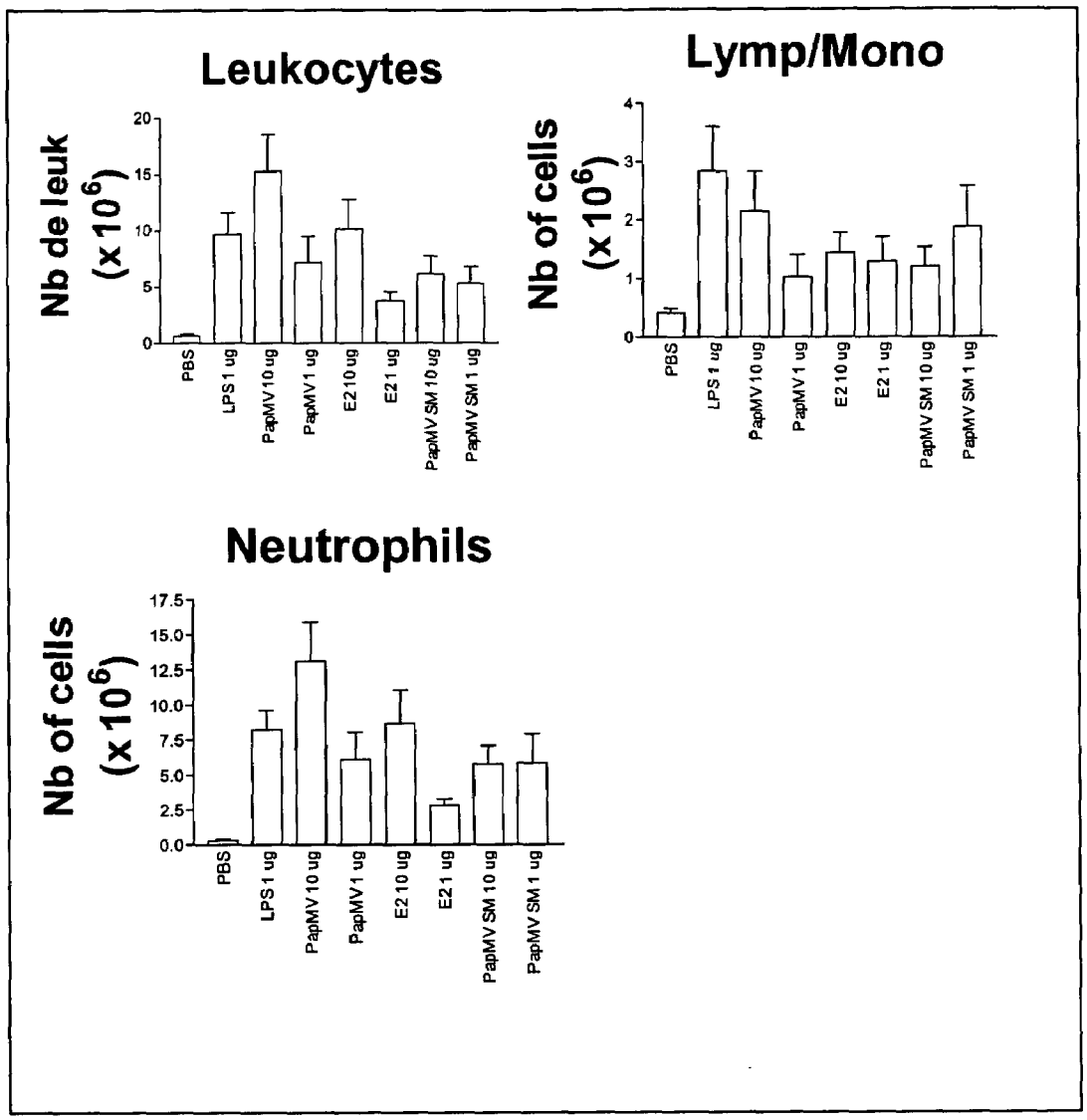
FIG. 4 illustrates the leukocyte accumulation induced by PapMV in the air pouch model.
Figure 5:
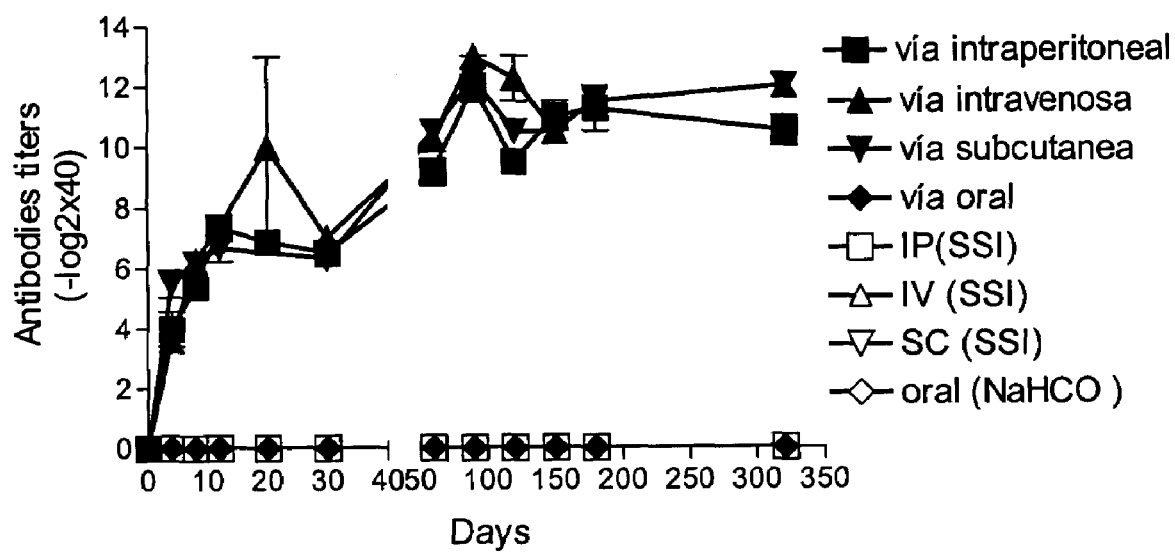
FIG. 5 illustrates the immune response to PapMV. Mice (6 for each concentration) that were injected IP once with PapMV or with ISS (Isotonic saline solution.
Figure 6:
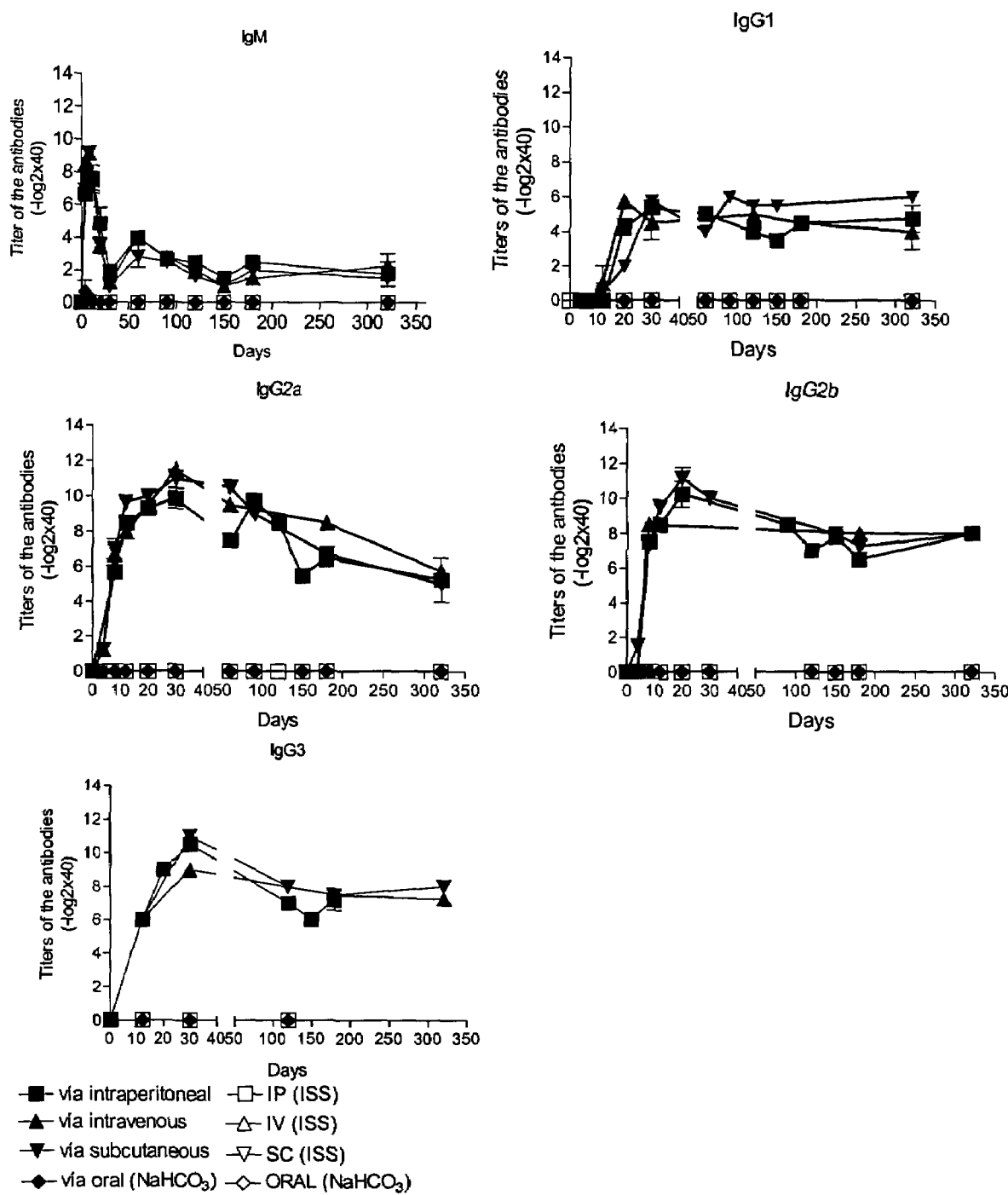
FIG. 6 illustrates an immune response to PapMV. Mice (6 for each concentration) that were injected IP once with PapMV or with ISS (Isotonic saline solution.
Figure 7:
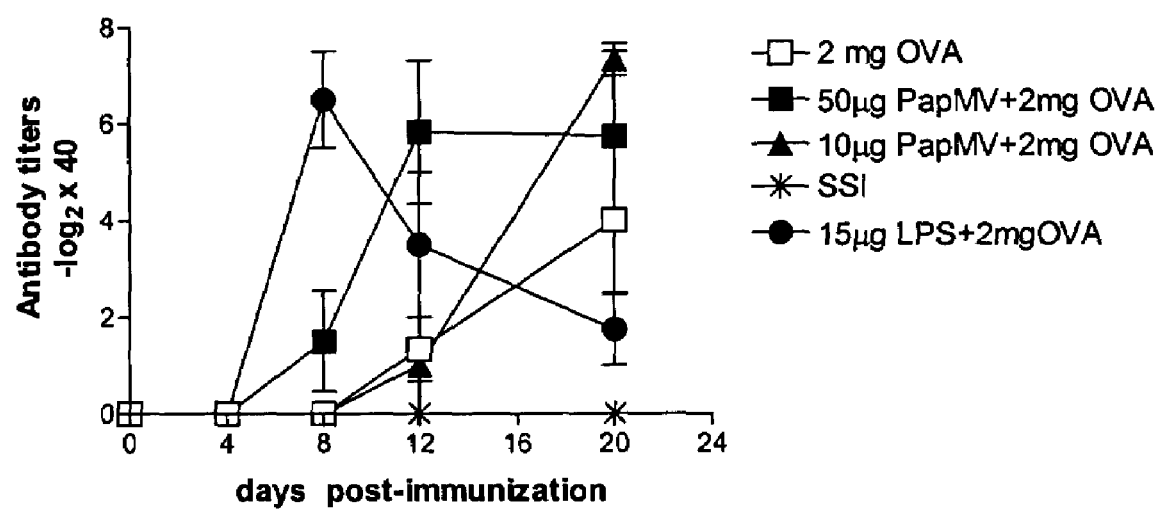
FIG. 7 illustrates an evaluation of the PapMV potency as adjuvant to ovabulmin.

The 2 epitopes chosen are found at the surface of the HCV virion. The E1 epitope (amino acid 285-303) and E2 epitope (amino acids 512-536), are shown to be strongly immunogenic in patients that have cleared the viral infection (David et al., 2001). PapMV was engineered to harbour at its C-terminus the fusion of the E1 and E2 peptide of HCV which, can assemble in PapMV virus like particles in vitro (FIG. 3).

Three epitopes that are found at the surface of the HCV virion of E1 and E2 outside of HVR-1 in conserved region of the viral envelope glycoproteins were chosen. An E1 epitope (amino acid 285-303) and 2 E2 epitopes (amino acids 512-536 and 528-546) were shown to be strongly immunogenic in patients that have cleared the viral infection. Furthermore, one E2 epitope (512-536) was shown to trigger the production of neutralizing antibodies that are found in the sera of patient that cleared the infection. These three regions are good candidates for the development of a HCV vaccine because they are conserved through HCV subtypes and strains and are located outside the hypervariable region of the envelope glycoproteins. The constructs PapMV-E1 and PapMV-E2 were expressed in *E.coli*. The recombinant proteins were purified and assembled in vitro. The assembly of the recombinant CP with the HCV E2 fusions generate rVLPs that are similar to the recombinant wt CP control except that they appear to be slightly larger because of the fusion.

Figure 8:
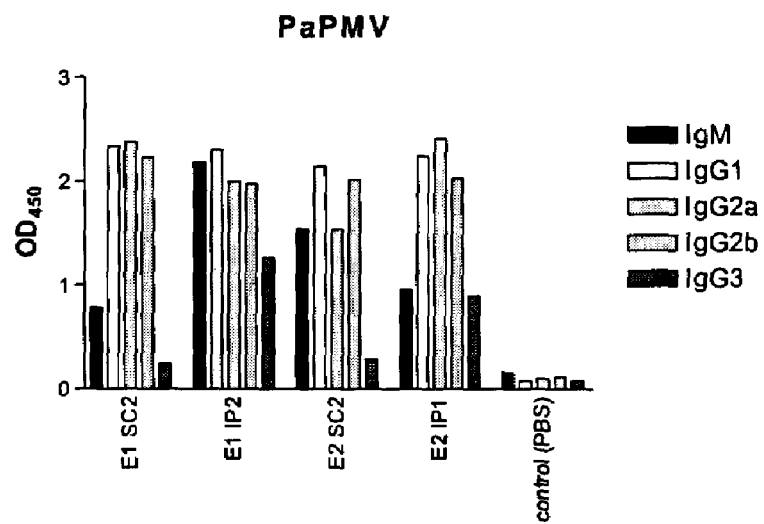
FIGS. 8A and 8B illustrate the characterization of the immune response to the PapMV and to HCV peptides derived from the HCV surface glycoprotein's E1 and E2.
Figure 8:
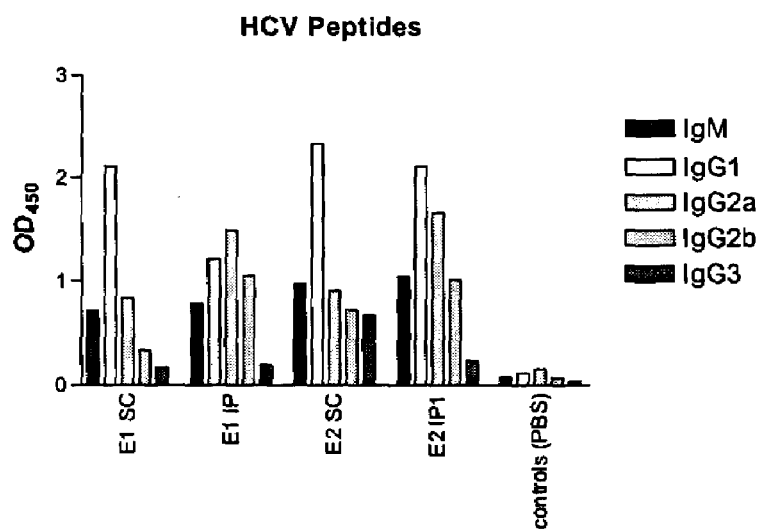
Figure 9:
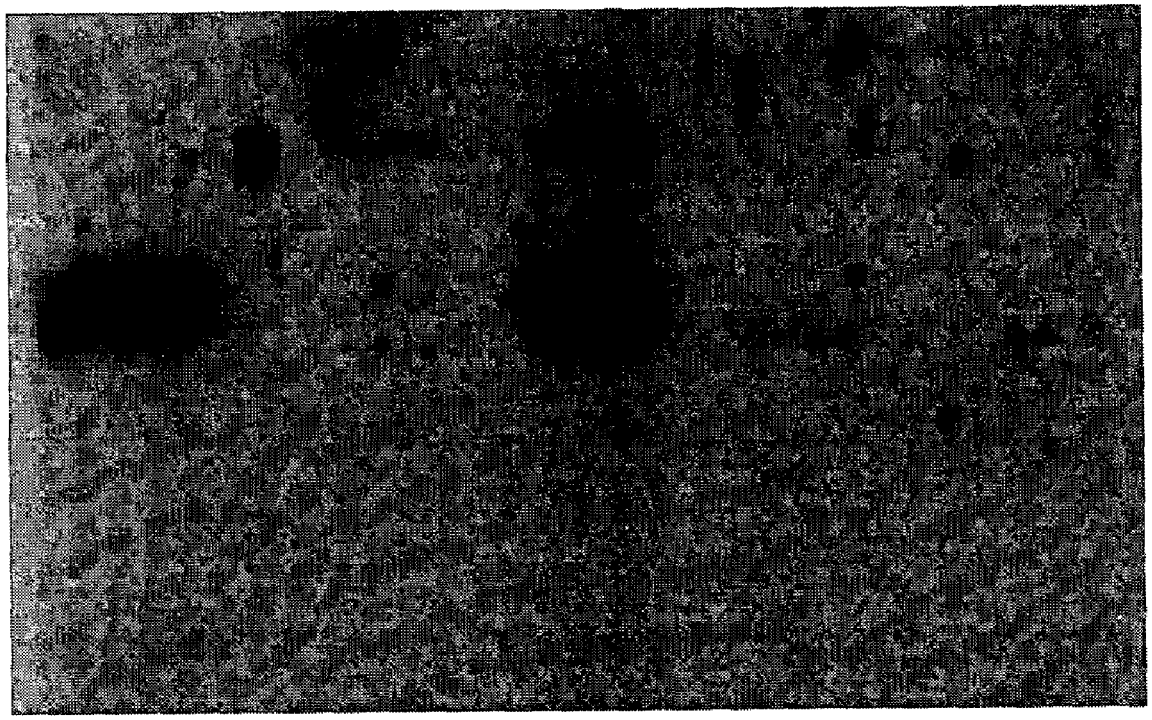
FIG. 9 illustrates Western blotting showing the specific migration of he PapMV CP to lymph node and spleen with an intraperitoneal injection.

Mice were immunized with the recombinant VLPs that were produced in vitro. LPS were removed using a polymixin column and injected in mice intraperetoneally and sub-cutaneously. We used 1, 10 and 100 αg of VLPs and three mice were injected for each treatment. The immune response to the peptide and to the PapMV was analysed by ELISA. It was observed that IgG were directed to the peptide as well as to the surface of the VLPs (FIG. 8). This result shows that recombinant PapMV can be used to trigger an excellent immune response at the surface of epitopes and used as vaccine without the help of adjuvant.

EXAMPLE IV

Immunization Against Thyphoid

Typhoid fever is an acute infection of the reticuloendothelial system, the intestinal lymphoid tissue and gall bladder that is caused by the bacteria *Salmonella typhii*. It is still worldwide a significant disease that affects more than 16 million persons from which, 600,000 do not survive to the infection. The majority of the infection affects children and young adults, and can be prevented by vaccination. Different types of vaccine are currently available: 1) Heat-inactivated, phenol-preserved whole-cell parental vaccine (Wyet-Ayerst) administrated intramuscularly or subcutaneously. 2) Acetone-inactivated and dried whole-cell parental vaccine. 3) Purified (non denatured) Vi polysaccharide parental vaccine (Aventis) that is administrated by injection into the deltoid. 4) Attenuated gal E, Vi-negative strain Ty21a, used as a live oral vaccine.

Inactivated parental bacteria (type 1-3) can lead to undesired immune responses because of the complexity of the lipopolysaccharide (LPS) and the number of presented antigens that elicit undesirable side effects. Furthermore, the Vi polysaccharides are thymus independent antigens (Robins and Robins, 1984) which were shown to have a good efficacy in the field trials but, are also known to be inefficient in inducing immunological memory. Several exposures to the antigen are needed to maintain the protection, making this approach appropriate only for travellers visiting endemic areas. The vaccines currently available are not adapted for people living permanently in contaminated areas. Vaccine based on attenuated bacteria (type 4) can cause nausea, vomiting and abdominal pain. It is also not recommended to administrate this vaccine to patients suffering from immunosuppression, intestinal diseases, diarrhea, taking antibiotics or to pregnant women and children less that 6 years old. This vaccine must be stored at 4° C. because it is sensitive to heat and should not be frozen. The sensitivity of ty21A to adverse conditions is problematic when you want to reach populations that live in poor countries under tropical climate which, are the regions most affected by typhoid.

A membrane protein from *S. typhii* called porin was shown to be a good immunogen because it elicits both antibody and cellular immune response in mice and humans and was able to protect mice against *S. typhi*. Porins are the most abundant protein on the membrane of Gram-negative bacteria that functions as passive diffusion channels for low molecular weight molecule. These proteins display a high degree of both structural and functional homology, and are therefore assumed to have a common ancestor. Two small epitopes corresponding to loop 6 and 7 of the *S. typhii* porin that are exposed to the surface of the bacteria were shown to be involved in protective mechanisms elicited by immunization with porins. Those regions are specific for *S.typhii* and are excellent epitope for the development of a recombinant subunit vaccine. We have cloned at the C-terminus of the PapMV CP loop 6 of the porin of *S. typhii*. The recombinant protein was purified and the PapMV virus like particles were produced in vitro with RNA as described before (FIG. 3F).

It is understood that the invention is not restricted to the above preferred embodiments, and that modifications are possible provided they are within the scope of the appended claims.

We claim:

1. A method of potentiating an immune response against an antigen comprising one or more B-cell antigenic epitopes and/or one or more T-cell antigenic epitopes in an animal, said method comprising the step of administering to said animal said antigen and an effective amount of an adjuvant, wherein said adjuvant is a papaya mosaic virus (PapMV), or a virus-like particle (VLP) comprising PapMV coat protein, said PapMV coat protein being capable of assembling to form said VLP, wherein said antigen is fused to the C-terminus of a coat protein of said VLP, such that said antigen is disposed on the outer surface of the PapMV or VLP, and wherein said immune response is a humoral and/or cellular response.

2. The method of claim 1, wherein said PapMV is a wild-type virus.

3. The method of claim 1, wherein said PapMV is a recombinant virus.

4. The method of claim 1, wherein said PapMV is a pseudovirus.

5. The method of claim 1, wherein said antigen is an immunogen.

6. The method of claim 1, wherein said antigen and said adjuvant are administered parenterally, enterally or orally to said animal.

7. The method of claim 1, wherein said immune response is systemic.

8. The method of claim 1, wherein said immune response is a mucosal immune response.

9. The method of claim 1, wherein said immune response is a humoral immune response.

10. The method of claim 1, wherein said immune response is a cellular immune response.

11. The method of claim 1, wherein said antigen is a viral, a bacterial or a parasitical protein, or fraction thereof.

12. The method of claim 1, wherein said antigen and said adjuvant are co-administered to said animal.

13. The method of claim 1, wherein said adjuvant is administered to said animal prior to administration of said antigen.

14. The method of claim 1, wherein said adjuvant is administered to said animal subsequent to administration of said antigen.

15. The method of claim 1, wherein said animal is a mammal, bird or fish.

16. The method of claim 15, wherein said animal is a mammal.

17. The method of claim 15, wherein said animal is a bird.

18. The method of claim 15, wherein said animal is a fish.

19. The method of claim 1, wherein said animal is a human.

20. The method of claim 1, wherein said one or more B-cell antigenic epitopes and/or one or more T-cell antigenic epitopes are hepatitis C virus antigenic epitopes or *Salmonella typhi* antigenic epitopes.

21. The method of claim 1, wherein said cellular response is a cytotoxic T lymphocyte response.

22. A method of potentiating a humoral and/or cellular immune response against an antigen comprising one or more B-cell antigenic epitopes and/or one or more T-cell antigenic epitopes in an animal, said method comprising the step of administering to said animal said antigen and an effective amount of an adjuvant, wherein said adjuvant is a virus-like particle (VLP) comprising PapMV coat protein, said PapMV coat protein being capable of assembling to form said VLP,
wherein said antigen is fused to the C-terminus of said PapMV coat protein.

23. The method of claim 22, wherein said antigen and said adjuvant are administered parenterally to said animal.

24. The method of claim 22, wherein said animal is a mammal.

25. The method of claim 22, wherein said animal is a human.

26. The method of claim 22, wherein said antigen is a viral, a bacterial or a parasitical protein, or fraction thereof.

27. The method of claim 22, wherein said one or more B-cell antigenic epitopes and/or one or more T-cell antigenic epitopes are hepatitis C virus antigenic epitopes or *Salmonella typhi* antigenic epitopes.

28. The method of claim 22, wherein said cellular immune response is a cytotoxic T lymphocyte response.

29. The method of claim 1, wherein said adjuvant is PapMV.

30. The method of claim 1, wherein said adjuvant is a VLP comprising PapMV coat protein and said antigen is fused at the C-terminus of said PapMV coat protein.

31. The method of claim 1, wherein said PapMV coat protein PapMV coat protein is a recombinant protein produced in *E. coli*.

32. The method of claim 1, wherein said PapMV coat protein is a recombinant protein produced in *E. coli*.

33. The method of claim 1, wherein said adjuvant is a VLP comprising PapMV coat protein.

34. The method of claim 9, wherein said humoral immune response is a long lasting antibody memory response.

35. The method of claim 22, wherein said humoral immune response is a long lasting antibody memory response.

* * * * *